United States Patent
Lussey et al.

(10) Patent No.: US 7,186,356 B2
(45) Date of Patent: Mar. 6, 2007

(54) ANALYTICAL DEVICE

(75) Inventors: David Lussey, Darlington (GB); David Bloor, Durham (GB); Paul Jonathan Laughlin, Houghton-Le-Spring (GB); Philip James Walton Hands, Durham (GB)

(73) Assignee: Peratech Ltd., Durham (GB)

( * ) Notice: Subject to any disclaimer, the term of this patent is extended or adjusted under 35 U.S.C. 154(b) by 382 days.

(21) Appl. No.: 10/479,745

(22) PCT Filed: May 30, 2002

(86) PCT No.: PCT/GB02/02523

§ 371 (c)(1),
(2), (4) Date: Dec. 5, 2003

(87) PCT Pub. No.: WO02/099822

PCT Pub. Date: Dec. 12, 2002

(65) Prior Publication Data

US 2004/0217331 A1   Nov. 4, 2004

(30) Foreign Application Priority Data

Jun. 7, 2001   (GB) ................. 0113905.4

(51) Int. Cl.
*H01B 1/00* (2006.01)
*H01C 8/00* (2006.01)
*H01C 10/14* (2006.01)

(52) U.S. Cl. .............. 252/500; 338/224; 338/318
(58) Field of Classification Search ............. 252/512; 338/34, 224; 73/53.01; 204/422, 228.1

See application file for complete search history.

(56) References Cited

U.S. PATENT DOCUMENTS 1,455,735 A   5/1923   Rojas ................... 338/8

(Continued)

FOREIGN PATENT DOCUMENTS

DE   38 05 887 C1   9/1989

(Continued)

OTHER PUBLICATIONS

Nickel Powder Type 287, "A filamentary powder with a characteristic three-dimensional chain-like network of very spiky beads".

(Continued)

*Primary Examiner*—Mark Kopec
*Assistant Examiner*—Jaison Thomas
(74) *Attorney, Agent, or Firm*—Stites & Harbison PLLC; Douglas E. Jackson

(57) ABSTRACT

A sensor for chemical species or biological species or radiation presenting to test fluid a polymer composition comprises polymer and conductive filler metal, alloy or reduced metal oxide and having a first level of electrical conductance when quiescent and being convertible to a second level of conductance by change of stress applied by stretching or compression or electric field, in which the polymer composition is characterized by at least one of the features in the form of particles at least 90% w/w held on a 100 mesh sieve; and/or comprising a permeable body extending across a channel of fluid flow; and/or affording in-and-out diffusion of test fluid and/or mechanically coupled to a workpiece of polymer swellable by a constituent of test fluid.

7 Claims, 16 Drawing Sheets

U.S. PATENT DOCUMENTS

| | | | |
|---|---|---|---|
| 2,042,606 A | 6/1936 | Kotowski | 252/511 |
| 2,375,178 A | 5/1945 | Ruben | 29/621 |
| 2,472,214 A | 6/1949 | Hurvitz | 338/44 |
| 2,951,817 A | 9/1960 | Myers | 252/511 |
| 3,056,005 A | 9/1962 | Larson | 200/86 R |
| 3,125,739 A | 3/1964 | Deibel et al. | 338/99 |
| 3,180,012 A | 4/1965 | Smith | 75/246 |
| 3,629,774 A | 12/1971 | Crites | 338/114 |
| 3,794,790 A | 2/1974 | Leyland | 200/86 R |
| 3,850,697 A | 11/1974 | Brown et al. | 29/623.1 |
| 3,875,434 A | 4/1975 | Harden et al. | 327/516 |
| 3,932,857 A | 1/1976 | Way et al. | 340/568.2 |
| 4,000,488 A | 12/1976 | Ephraim | 340/568.2 |
| 4,028,276 A | 6/1977 | Harden et al. | 252/873 |
| 4,054,540 A | 10/1977 | Michalchik | 252/512 |
| 4,120,828 A | 10/1978 | Michalchik | 252/513 |
| 4,137,494 A * | 1/1979 | Malley et al. | 324/450 |
| 4,138,369 A | 2/1979 | Arai et al. | 252/512 |
| 4,145,317 A | 3/1979 | Sado et al. | 252/512 |
| 4,258,100 A | 3/1981 | Fujitani et al. | 428/316.6 |
| 4,292,261 A | 9/1981 | Kotani et al. | 264/437 |
| 4,481,808 A | 11/1984 | Sakata et al. | 73/61.47 |
| 4,529,959 A | 7/1985 | Ito et al. | 338/295 |
| 4,610,808 A | 9/1986 | Kleiner | 252/512 |
| 4,631,952 A * | 12/1986 | Donaghey | 73/25.03 |
| 4,748,433 A | 5/1988 | Jackson et al. | 338/6 |
| 4,772,878 A | 9/1988 | Kane | 340/568.4 |
| 4,790,968 A | 12/1988 | Ohkawa et al. | 264/104 |
| 4,961,064 A * | 10/1990 | Hara | 338/231 |
| 5,060,527 A | 10/1991 | Burgess | 73/862.68 |
| 5,106,540 A * | 4/1992 | Barma et al. | 252/511 |
| 5,213,715 A | 5/1993 | Patterson et al. | 252/518 |
| 5,237,307 A | 8/1993 | Gritton | 340/572.1 |
| 5,393,597 A | 2/1995 | Childers et al. | 442/110 |
| 5,406,263 A | 4/1995 | Tuttle | 340/572.1 |
| 5,512,882 A | 4/1996 | Stetter et al. | 340/632 |
| 5,589,222 A | 12/1996 | Thometzek et al. | 427/215 |
| 5,591,382 A | 1/1997 | Nahass et al. | 252/511 |
| 5,643,502 A | 7/1997 | Nahass et al. | 252/511 |
| 5,651,922 A | 7/1997 | Nahass et al. | 252/511 |
| 5,686,158 A | 11/1997 | Gibbon | 428/36.92 |
| 5,962,118 A | 10/1999 | Burgess | 428/308.4 |
| 5,965,064 A | 10/1999 | Yamada et al. | 252/512 |
| 6,194,769 B1 | 2/2001 | Martin et al. | 257/414 |
| 6,291,568 B1 | 9/2001 | Lussey | 524/413 |
| 6,335,077 B1 | 1/2002 | Tani et al. | 386/88 |
| 6,495,069 B1 * | 12/2002 | Lussey et al. | 252/512 |
| 6,646,540 B1 * | 11/2003 | Lussey | 338/47 |
| 2002/0149466 A1 * | 10/2002 | Sunshine et al. | 338/34 |

FOREIGN PATENT DOCUMENTS

| | | |
|---|---|---|
| EP | 0 177 267 | 4/1986 |
| EP | 0 260 330 | 3/1988 |
| EP | 0 289 193 A1 | 11/1988 |
| GB | 1073347 | 6/1967 |
| GB | 1142254 | 2/1969 |
| GB | 2 054 277 A | 2/1981 |
| GB | 2 343 516 A | 5/2000 |
| RU | 2 082 239 C1 | 6/1997 |
| WO | WO 94/14142 | 6/1994 |
| WO | WO 01/88935 A1 | 11/2001 |

OTHER PUBLICATIONS

Nickel Powder Type 123, "A powder of equiaxed shape with a spiked, irregular surface".

* cited by examiner

| Polymer / Solvent | Silicone (Alpha 153) | Polyurethane (Techsil) | Polyvinylalcohol |
|---|---|---|---|
| Ethanol | 30s: $1.14 \times 10^{-3} \rightarrow 4.40 \times 10^{-2}$<br>60s: $3.63 \times 10^{-2} \rightarrow 0.251$<br>Saturation: 6.3 | 30s: 0.167<br>60s: 0.811<br>Saturation: $1.2 \times 10^6$ | 30s: $3.02 \times 10^{-2}$<br>60s: $9.67 \times 10^{-2}$<br>Saturation: $> 4.8 \times 10^4$ |
| Hexane | 30s: 4.47<br>60s: 27.2<br>Saturation: $> 7.5 \times 10^8$ | 30s: 281<br>60s: $> 4.5 \times 10^4$<br>Saturation: $>> 4.5 \times 10^4$ | 30s: $1.19 \times 10^{-2}$<br>60s: $3.16 \times 10^{-2}$<br>Saturation: 1.6 |
| Tetrahydrofuran | 30s: $0.192 \rightarrow 4.72$<br>60s: $0.731 \rightarrow 71.6$<br>Saturation: $6.3 \times 10^3$ | 30s: $9.80 \times 10^{-2}$<br>60s: 0.897<br>Saturation: $3.7 \times 10^5$ | 30s: $6.22 \times 10^{-2} \rightarrow 1.81$<br>60s: 3.95<br>Saturation: $> 3.3 \times 10^4$ |
| Water | 30s: $0 \rightarrow 1.54 \times 10^{-3}$<br>60s: $4.99 \times 10^{-3} \rightarrow 9.83 \times 10^{-3}$<br>Saturation: $3.1 \times 10^{-2}$ | | |

*Fig. 6 - Table*

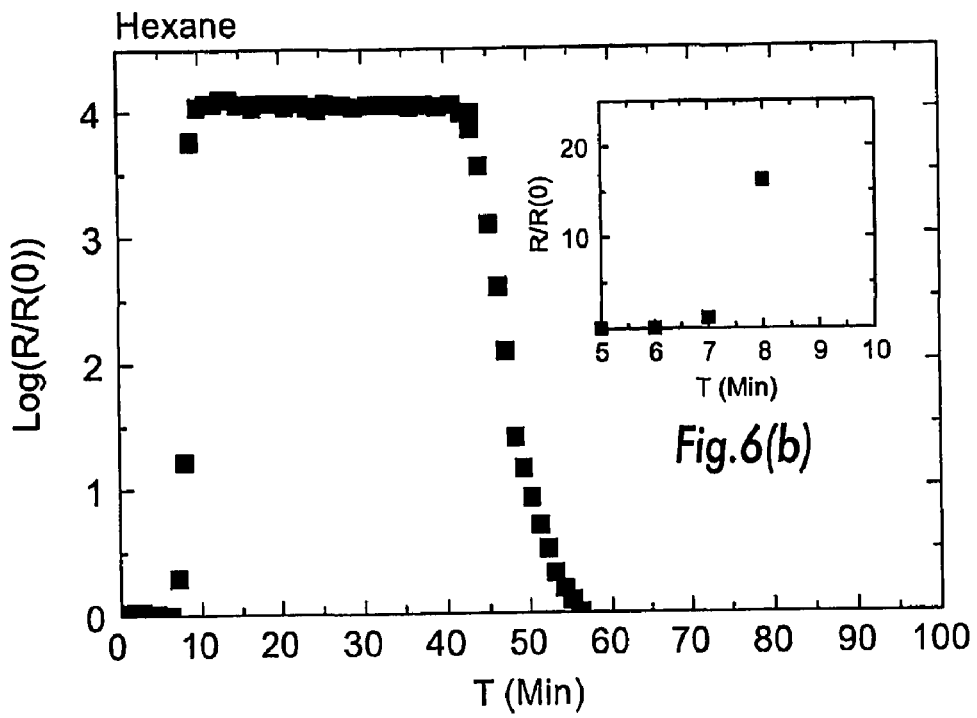
Fig.6(a)
Fig.6(b)
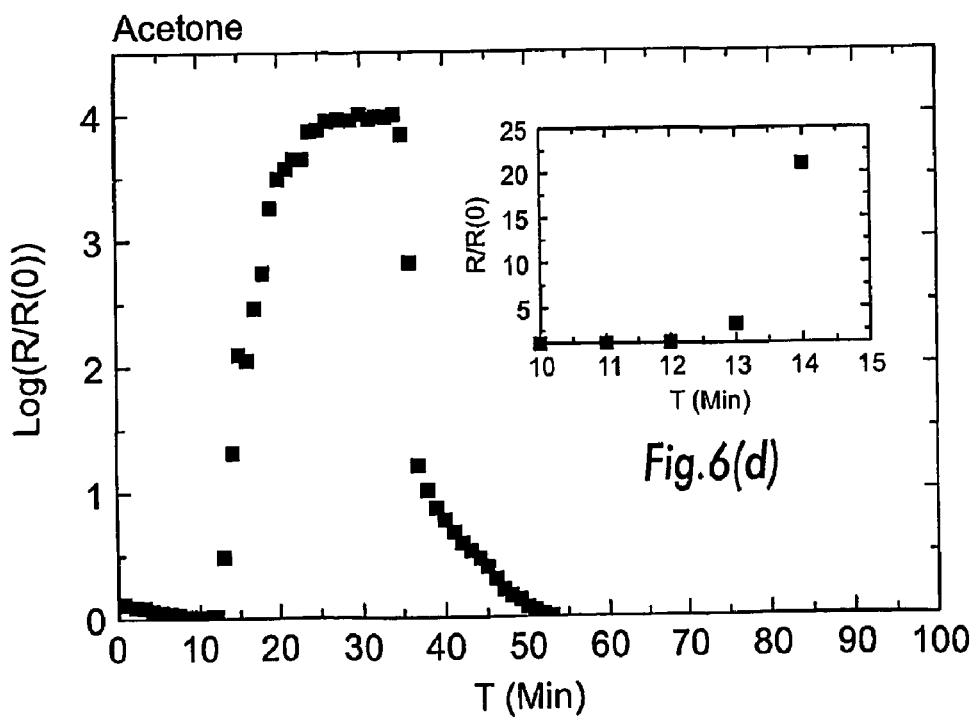
Fig.6(c)
Fig.6(d)

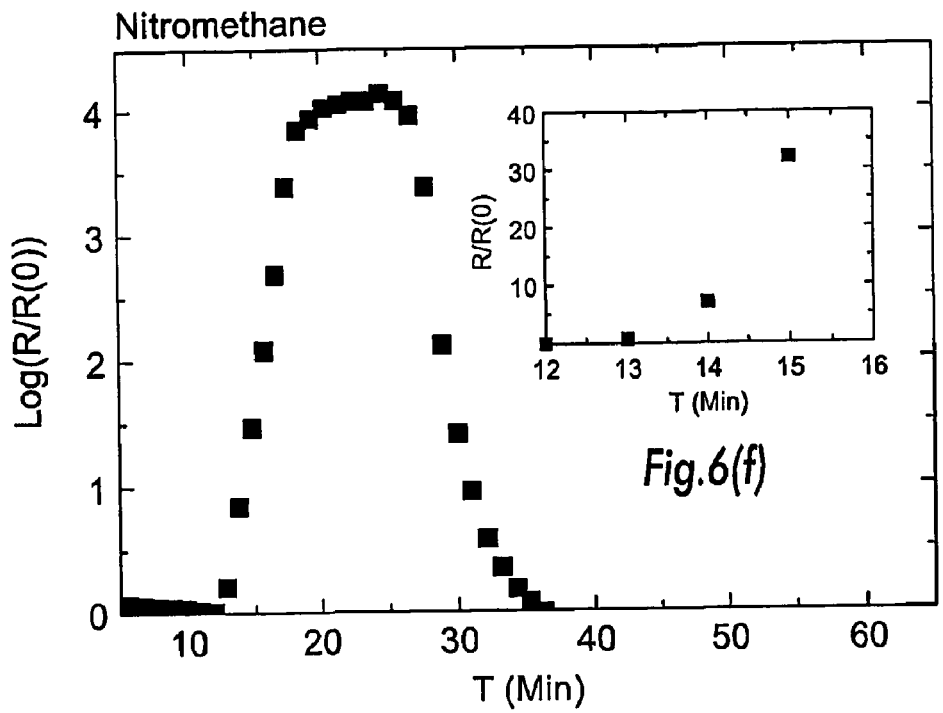
*Fig.6(e)*
*Fig.6(f)*
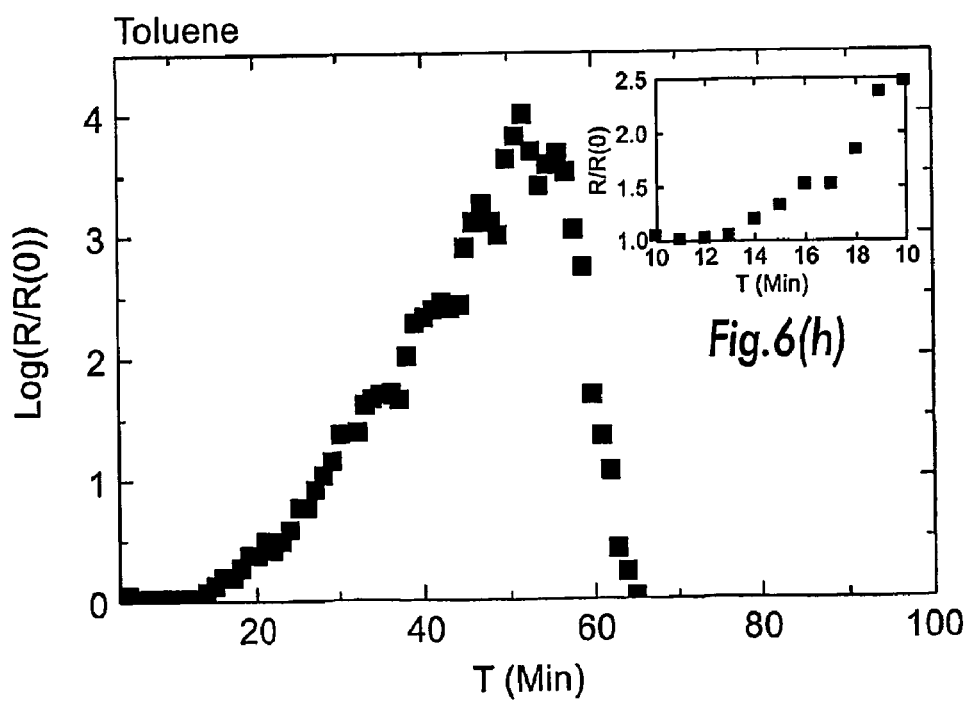
*Fig.6(g)*
*Fig.6(h)*

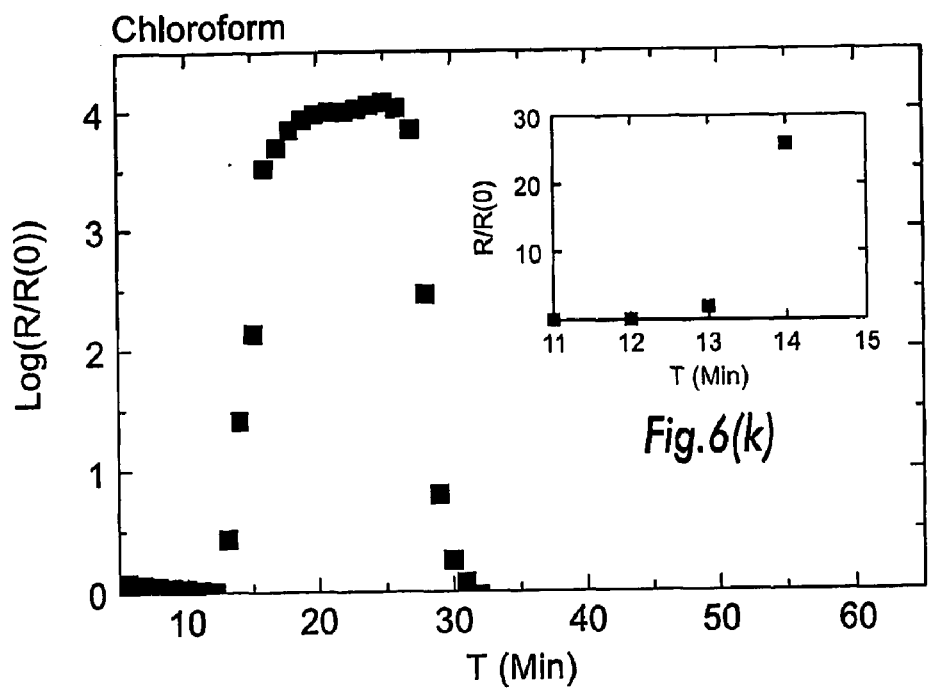
Fig.6(i)
Fig.6(k)
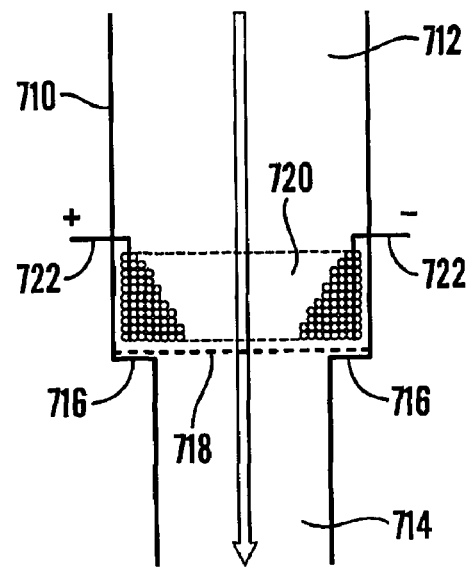
Fig.7

ANALYTICAL DEVICE

TECHNICAL FIELD

This invention relates to an analytical device, especially a sensor for detecting and measuring quantities of materials in fluid form.

Known sensors based on a compressible polymer element containing conductive filler and depending on 'percolation', that is, electrical contact between filler particles, are subject to various limitations, especially limited range of variation of electrical conductance.

PCT application PCT/GB00/02402 published as WO 00/79546 discloses a sensor for chemical species or biological species or radiation comprising:
  a) a contacting head presenting a polymer composition comprising at least one substantially non-conductive polymer and at least one electrically conductive filler and being electrically insulating when quiescent but conductive when subjected to mechanical stress or electrostatic charge;
  b) means for access of a test specimen to the head;
  c) means to connect the head into an electrical circuit effective to measure an electrical property of the polymer composition.

The expression 'polymer composition' will be used herein to mean one containing polymer and conductive filler particles of metal, alloy or reduced metal oxide, and having a first level of electrical conductance when quiescent and being convertible to a second level of conductance by change of stress applied by stretching or compression or electric field. More details of compositions of this type are available in PCT applications GB98/00206 and GB99/00205, published respectively as WO 98/33193 and 99/38173, the disclosures of which are incorporated herein by reference.

We have now found advantageous sensors in which the properties of the polymer composition can be put to practical effect. In general, the preferred or optional features set out in PCT/GB00/002402 can be used in conjunction with the sensors according to the invention, in particular:

in the polymer composition the encapsulant polymer phase is highly negative on the triboelectric series, does not readily store electrons on its surface and is permeable to a range of gases and other mobile molecules into the head and/or onto its surface, thus changing the electrical property of the polymer composition.;

the contacting head may include stressing means, for example mechanical compressing or stretching or bending or a source of electric or magnetic field, to bring the polymer composition to the level of conductance appropriate to the required sensitivity of the sensor;

the sensor may afford static or dynamic contacting. For static contacting it may be a portable unit usable by dipping the head into the specimen in a container. For dynamic conducting, it may be supported in a flowing current of specimen or may include its own feed and/or discharge channels and possibly pump means for feeding and or withdrawing specimen. Such pump means is suitably peristaltic as, for example in medical testing;

the properties of the system may change in real time, for example in controlling an engine or chemical process or atmospheric quality;

in a preferred sensor the polymer composition may be excited by a linear or non-linear AC field. A range of techniques may be used to distinguish the signal of interest from noise and from interfering signals, for example— reactance, inductance, signal profile, phase profile, frequency, spatial and temporal coherence;

in another example the polymer composition is held in a transient state by application of an electrostatic charge; then increased ionisation as a consequence of exposure to nuclear radiation changes the electrical resistivity, reactance, impedance or other electrical property of the system;

in a further example a complexing ionophore or other lock and key or adsorbing material is incorporated within the polymer composition. Such materials include crown ethers, zeolites, solid and liquid ion exchangers, biological antibodies and their analogues or other analogous materials. When excited by a DC, linear AC or non-linear AC field, such materials change their electrical property in accordance with the adsorption of materials or contact with sources of radiation. Such materials offer the potential to narrow the bandwidth for adsorbed species and selectivity of the system. In a yet further example an electride, that is a material in which the electron is the sole anion, a typical example of which might be caesium-15-crown-5 prepared by vaporising caesium metal over 15-crown-5, is incorporated within the polymer composition. Other ionophore, zeolite and ion exchange materials might be similarly employed. Such a composition has a low electron work function, typically <<1 electron-volt, such that low DC or non-uniform AC voltages switch it from insulative to conductive phase with decreasing time constant and increasing the bandwidth for adsorbed species and of the system. Such materials may be used to detect the presence of adsorbed materials and or radiation sources.

SUMMARY OF THE INVENTION

According to the present invention there is provided a sensor for chemical species or biological species or radiation presenting to a test fluid a polymer composition comprising polymer and conductive filler particles of metal, alloy or reduced metal oxide and having a first level of electrical conductance when quiescent and being convertible to a second level of conductance by change of stress applied by stretching or compression or electric field, in which the polymer composition is characterised by at least one of the features:
  (a) in the form of particles at least 90% w/w held on a 100 mesh sieve; and/or
  (b) comprising a permeable body extending across a channel of fluid flow and/or affording in-and-out diffusion of test fluid and/or
  (c) mechanically coupled to a workpiece of polymer swellable by a constituent of test fluid.

In aspect (a) preferably the particles are at least 90% held on a 50 mesh sieve. For most purposes they pass an 18, possibly a larger e g 10, mesh sieve. They appear to be approximately spherical, of average diameter over 150, especially over 300, microns, and usually up to 1, possibly 2, mm. They may be used with advantage in embodiments of the invention in aspects (b) and (c). Preferred forms of the particles are described below.

The particles may be random-packed in a containing vessel without or with mutual adhesion, or supported on a yieldable framework such as foam or textile.

In aspects (a) and (b) the response of the sensor is due to the effect of the species or radiation on the polymer of the polymer composition or of a supporting framework. Preferably this effect is swelling of the polymer widening the separation between the conductive filler particles and thus a decrease in electrical conductance. Such widening lengthens the path of electrons through the polymer coating on the filler particles and thus decreases quantum tunnelling conductance.

In aspect (c) the effect of the mechanically coupled workpiece is to compress the polymer composition, thus decreasing the separation between filler particles, shortening the electron path and increasing tunnelling conductance. The workpiece may act as a mechanical member, for example a piston or lever; instead or in additional it may be may act randomly, for example as particles mixed with particles of the polymer composition. Evidently the operation of aspect (c) can oppose the operation of (a) or (b); this is, however, applicable in specialised conditions.

Each sensor includes means for ohmic connection of the polymer composition to an electrical circuit. To match the very long curve of conductance versus applied stress, the circuit preferably includes field-effect-transistors and logarithmic amplification. To distinguish analytes by rate of change of conductance, differential circuitry may be used. Ohmic connection can be conveniently provided by enclosing a permeable block of polymer composition between grids wholly or partly of ohmic conductive material, for example metal, or light metal mesh backed by plastic or ceramic, or metallised ceramic. If the polymer composition is in sheet form stretched across the channel, spaced ohmic conductors may be for example mechanically held in contact with it or formed on it as a coating such as a metal-rich paint or vapour-deposited layer. Intermediate and/or external conductors, ohmic or not, may comprise a pre-stressed polymer composition, possibly on a polymer or textile support.

Each sensor according to aspect (a) or (b) further includes means to stress the polymer composition to an initial level of electrical conductance susceptible to measurable change as a result of contact with the test fluid. This is conveniently provided by compressing the body by disposing the body in a tube between grids and squeezing the grids together, suitably by the action of an internal sleeve slidable telescope-wise in the tube, possibly using a micrometer. For sheet form composition stressing is suitably by stretching by a sock-donning action or by bending unsupported or supported e g over a former or by deforming a disc to a shallow cone or spheroid.

For each the polymer composition may be stressed before contacting. This may be effected for example by suitable formulation of the composition such as mixing in presence of a volatile liquid removal of which compresses the composition to conductance. In another method its stress/resistance response may be measured after contacting and compared with a standard, typically the same or a duplicate head in equilibrium with blank fluid. Mechanical means of pre-stressing may be for example screw, hydraulic, piezo-electric, magnetic and thermal expansion e g using a bimorph.

A preferred composition is in the form of particles coated with polymer. The coating may be shrunk-on, possibly with compression sufficient for pre-stress to conduction. The particles may be for example granules as described herein, agglomerates thereof or comminuted bulk composition. The coating is permeable to analytes to which the sensor is to be applied. It is also thin enough to permit electrical conduction by quantum tunnelling as described below or, possibly at greater thickness, by conductive filler such as in the composition and/or carbon. The shrunk-on polymer is suitably a thermoset, for example epoxy, maleimide or 3-dimensional olefin resin.

The pre-stressed particles may be used in a loose-packed bed as in FIG. 1(a), 3(c) or 4(d) below. Conveniently they may adhere together, possibly with mild compression, in a shaped unit as in FIG. 7 below. Thus a series of units may be set up, differing in analyte response but interchangeable in the sensor structure.

For aspect (c) the option is available to start at non-conductance or 'start-resistance' as an alternative to initial stressing to conductance, and use the swelling of the polymer element to produce or increase conductance in the polymer composition.

Instead of or in addition, each sensor may be brought to the first level of conductance by an applied voltage and/or an electrostatic or radiative or magnetic field. The first level of conductance of the polymer composition is preferably substantially zero or at a low value ('start-resistance') sufficient to indicate that the sensor is in circuit.

The sensor may be used in combination with external means to modify its response. For example the fluid may be contacted, upstream of the head, with a sorbent effective to remove one trace material, leaving another to be determined by the sensor. In a particular embodiment the sorbent may be disposed close to the sensor head, thus avoiding a separate treatment step. Conversely a sorptive source of co-determinable material may be used. Drying and (respectively) humidification are examples.

In another example, suitable for very low concentrations of trace material, such a sorbent may be used to take up and store the whole amount of such material over a time period, then heated to desorb the material and pass it to the sensor.

Combination set-ups used in analysis may include, for example:

means to inject a known content of a known trace material, e g for calibration or co-sorption;
two sensors in parallel, one calibrated as reference;
an array of two or more sensors in series or parallel, for simultaneous detection of different trace materials;
a series succession of separately wired sensors constituting a chromatographic column;
supply of blank fluid, with changeover switching, to regenerate the sensor;
local heating to change specificity or assist regeneration; for this purpose the polymer composition or swellable polymer or sorbent may contain a heating coil or the polymer composition may be heated by feeding electricity to it up to its PTC temperature;
a substantial number of devices in parallel, with fluid changeover switching, to afford longer time for regeneration if required;
miniaturisation;
feedback control of stress levels;
computerised recording, comparing, transmitting.

Swellable polymers in aspect (c) and sorbents used to modify the response of the sensor may be selected from for example:

Structure-Wise:
compressed, sintered or bonded particulate;
coatings on high-surface support such as honeycomb or foam or textile;
ion-exchange resins;
chromatographic agents;

Chemical Composition:
chosen according to solubility parameter or chemical reactivity, for example for hydrocarbons, oxygenated hydrocarbons, acidics, basics, water, viruses, bacteria.

Any of the sensors may of course be used to determine the presence of an analyte or register the absence of an analyte that ought to be present.

In the polymer composition the metal, alloy or reduced metal oxide may be for example in one or more of the following states:

(i) on a resilient polymer structure 'naked', that is, without pre-coat but possibly carrying on its surface the residue of a surface phase in equilibrium with its storage atmosphere or formed during incorporation with the polymer;

(ii) on a resilient polymer structure carrying a thin coating of a passivating or water-displacing material or the residue of such coating formed during incorporation. This is similar to (i) but may afford better controllability in manufacture;

(iii) on a resilient polymer structure very thinly polymer-coated so as to be conductive when unstressed This is exemplified by granular nickel/polymer compositions of so high nickel content that the physical properties of the polymer are weakly if at all discernible. As an example, for nickel starting particles of bulk density 0.85 this corresponds to a nickel/silicone volume ratio (tapped bulk:voidless solid) typically well over about 10. Material of form (iii) can be applied to the resilient structure in aqueous suspension. The polymer may or may not be an elastomer. Form (iii) also affords better controllability in manufacture than (i);

(iv) polymer-coated but conductive only when stressed. This is exemplified by nickel/polymer compositions of nickel content lower than for (iii), low enough for physical properties of the polymer to be discernible, and high enough that during mixing the nickel particles and liquid form polymer become resolved into granules rather than forming a bulk phase. The relatively large granules preferred may be obtained by suitable control of mixing conditions, possibly with sieving and re-work of undersize An alternative would be to use particles made by comminuting material as in (v) below. Unlike (i) to (iii), material (iv) can afford a response to deformation within each individual granule as well as between granules, but ground material (v) is less sensitive. Material (iv) can be handled in aqueous suspension;

(v) embedded in bulk phase polymer, i e with sufficient polymer present to form a continuous polymer structure. This can be made by single-stage mixing or by mixing material (iv) with further polymer of the same or different type. Like (iv), material (v) is conductive only when stressed.

The general definition of the preferred polymer composition exemplified by (iv,v) is that it exhibits tunnelling conductance when stressed. This is particularly a property of polymer compositions in which a filler selected from powder-form metals or alloys, electrically conductive oxides of said elements and alloys, and mixtures thereof are in admixture with a non-conductive elastomer, having been mixed in a controlled manner whereby the filler is dispersed within the elastomer and remains structurally intact and the voids present in the starting filler powder become infilled with elastomer and particles of filler become set in close proximity during curing of the elastomer. Preferred conductive filler particles have a secondary structure including a spiky or dendritic surface texture, evident from a bulk density less than one third of their solid density before incorporation into the polymer composition. Polymer compositions exhibiting tunnelling conductance are the Quantum Tunnelling Composites available from PERATECH LTD, Darlington, England, under the trade name 'QTC'.

For a sensor available for more than one determination, the polymer composition is reversibly convertible between the levels of electrical conductance. However, in specialised uses this may not be necessary: then the composition may be non- or incompletely-convertible.

The invention includes items characteristic of its aspects, such as may be separately marketable, especially the QTC elements described with reference to the drawings.

BRIEF DESCRIPTION OF THE DRAWINGS

FIG. 6 shows graphically and in a Table the response of 3 sensors to various analytes.

FIG. 7 shows in sectional elevation a sensor in which the test sample flows through an immobilised bed of aggregates of polymer composition granules pre-stressed to conductance by shrunk-on thermoset;

In these drawings, where a fluid flow direction is indicated, this is for convenience of description, not for technical limitation.

DESCRIPTION OF THE PREFERRED EMBODIMENTS

Figure 1A:
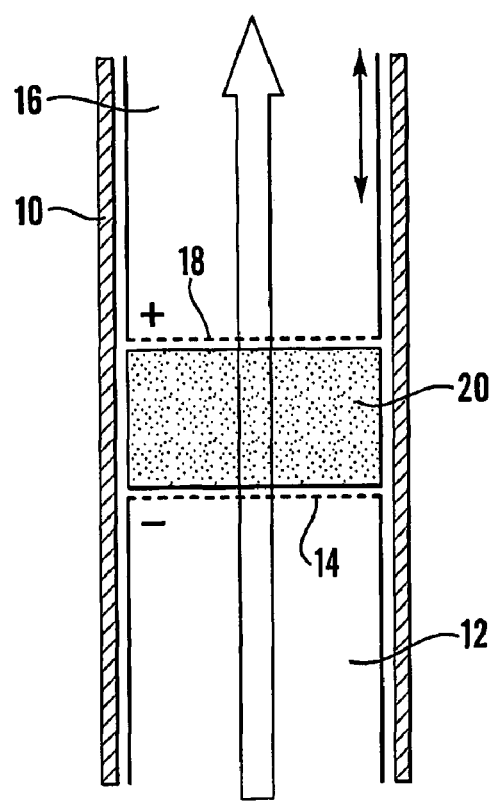
FIG. 1 shows in sectional elevation examples of a sensor in which the test sample flows through the polymer composition.

Referring to FIG. 1(a), the contacting head comprises fluid flow tube 10 presenting an internal surface inert to the fluid to be contacted and electrically insulating, at least in a region to be described. At the lower end of tube 10 is tube 12 fixed in position by means not shown and formed at its upper end with rigid grid 14. Tube 12, at least at the periphery of grid 14, fits fluid-tightly within tube 10. At the upper end of tube 10 is slidable tube 16, which is movable up or down by fine-adjustable means such as a micrometer (not shown), and is formed with rigid grid 18 suitably made of frit or gauze. Like tube 12, tube 16 fits fluid-tightly within tube 10. Grids 14 and 16 are electrically conductive, at least on the side respectively upwards and downwards and act as electrodes connected (by means not shown) to an external electrical circuit. The grids may thus be made of metal, such as a metal, for example as woven wire, foam or sinter, or metallised polymer or ceramic. The grids and the surrounding region of tube 10 enclose a fluid-permeable body 20 of QTC nickel/silicone polymer composition insulating when quiescent but conductive when compressed, to an extent dependent on the extent of compression. Body 20 may comprise for example random-pack granules, possibly mutually adhering, of the composition or a structure such as foam or cloth formed of or containing such composition.

To use the sensor, a steady flow of reference fluid, for example dry pure air or of pure water, is set up; then tube 16 and thus also grid 18 is adjusted downwards until the external circuit registers a change in resistance from a starting value to a lower value due to conduction by the polymer composition. Then the fluid is changed to the sample to be analysed. Resistance is measured allowing time to reach a steady state.

Figure 3A:
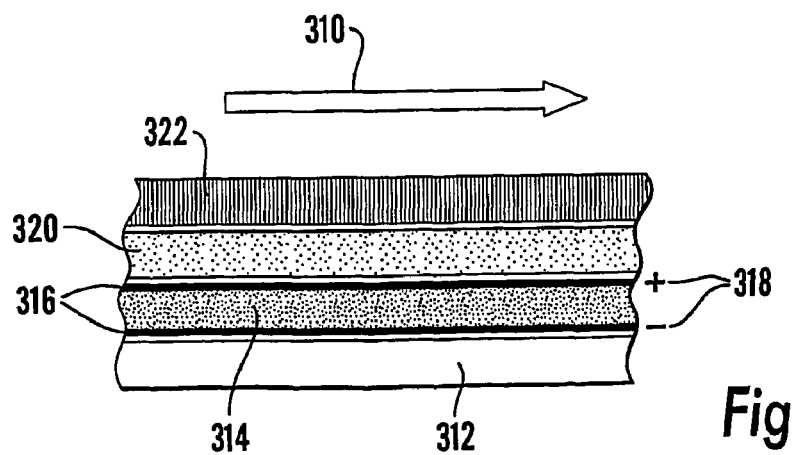
FIG. 3 shows in sectional elevation sensors in which the test sample acts on a swellable polymer member, which in turn applies a stress to the polymer composition.
Figure 3B:
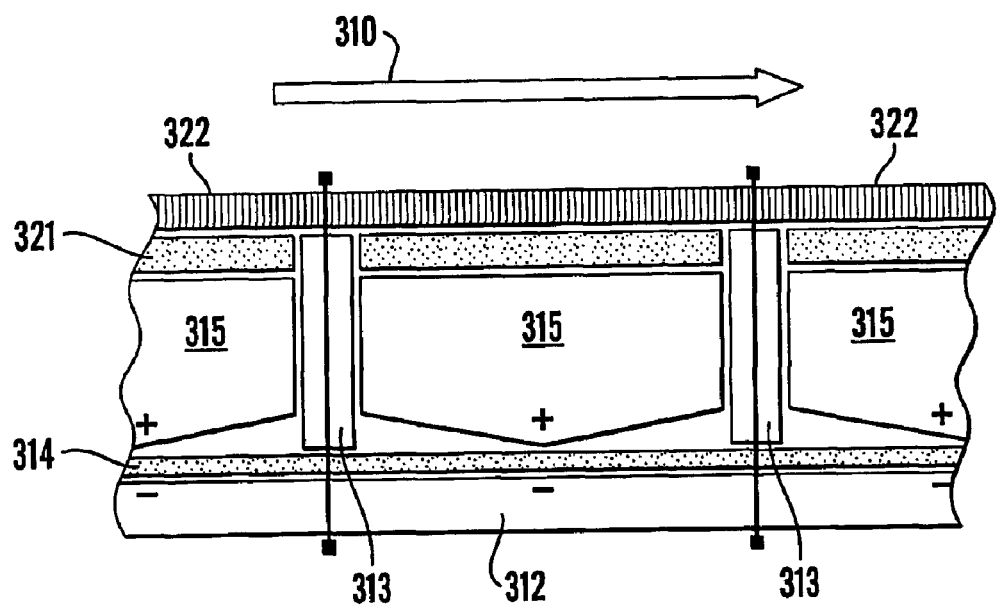
Figure 3C:
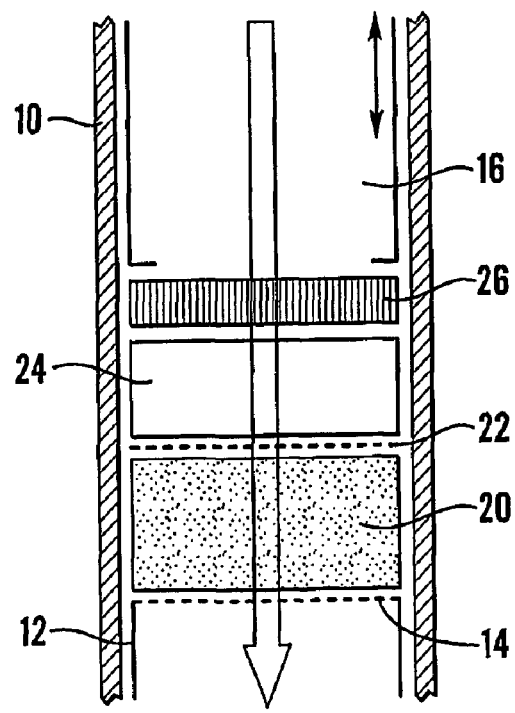

A modified version of this sensor is shown in FIG. 3(c) below.

Figure 1B:
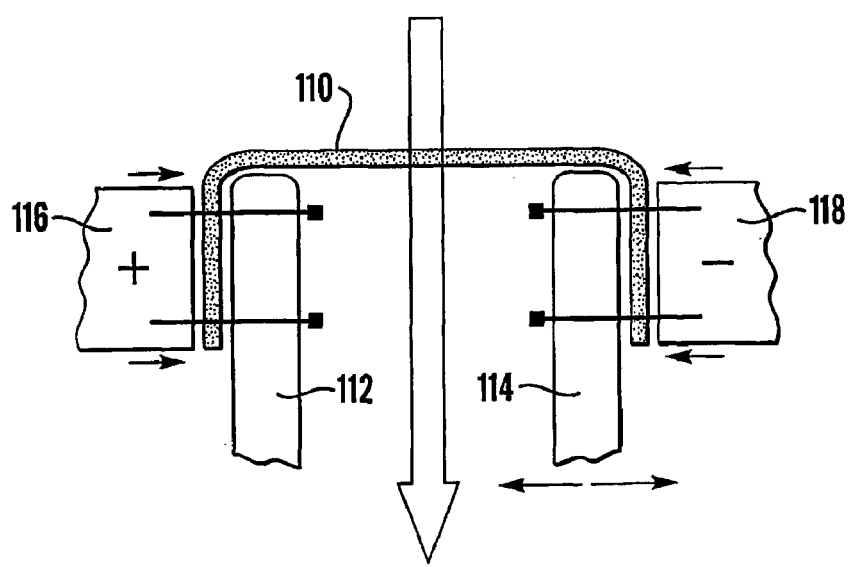

Referring to FIG. 1(b), the head is in fluid-tight contact at the outlet end of a fluid-flow tube (not shown) and presents to the tube the central portion of sheet 110 of QTC material, which is self-supporting as a result of initial nickel/silicone ratio or of dispersion of nickel-rich nickel/silicone granules in a fluid-permeable support membrane or e g textile or foam and may be micro-perforated to ease fluid flow. Sheet 110 is supported from its underside by mutually insulated round-ended members 112 (fixed) and 114 (adjustable horizontally), over which it extends externally and to which it is fixed by clamps 116 and 118, which are electrically conductive and act as electrodes. The distance between members 112 and 114 is adjustable by means not shown to stretch sheet 110 to give a level of electrical conductance appropriate to the sensitivity required. Sheet 110 is conveniently rectangular, to simplify the stretching mechanism.

Figure 1C:
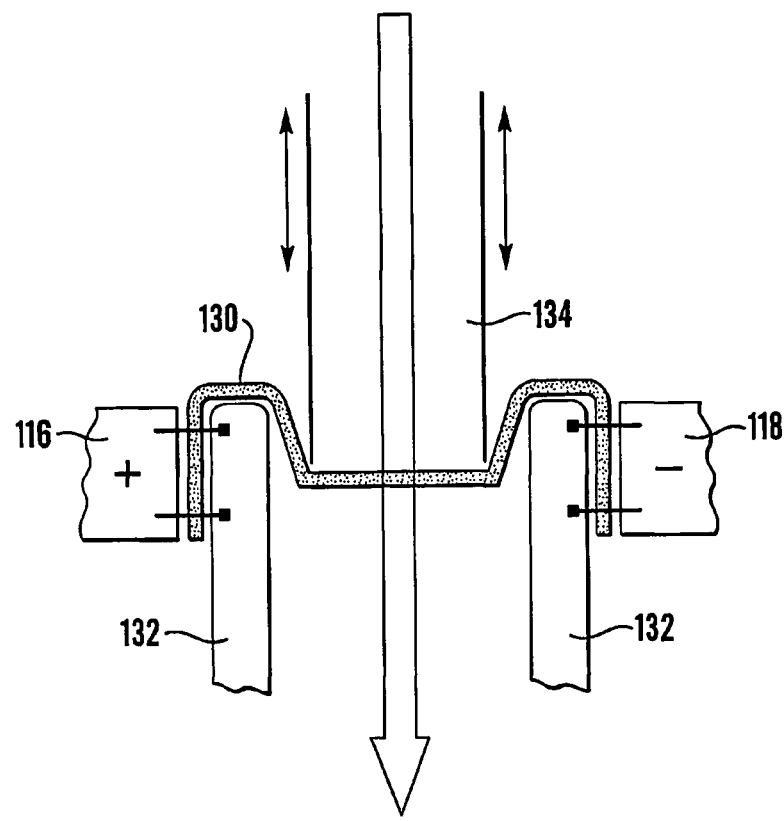

Referring to FIG. 1(c), in a modification of the device of 1(b) the sheet 130 of QTC material has a dished profile and is supported between members 132, which are not mutually adjustable and conveniently represent a diametral section of a tube such as a hollow cylinder. Members 132 are mutually insulated by being made of or coated with insulator or being parts of a split cylinder. Stretching of sheet 130 is by downwardly advancing fluid flow tube 134 into the dished portion of sheet 130. Tube 134 and members 132 are co-axial.

In the sectional elevations of FIG. 2, items 266, 267, 274 and 276 are, for the sake of clarity, shown unshaded.

Figure 2A:
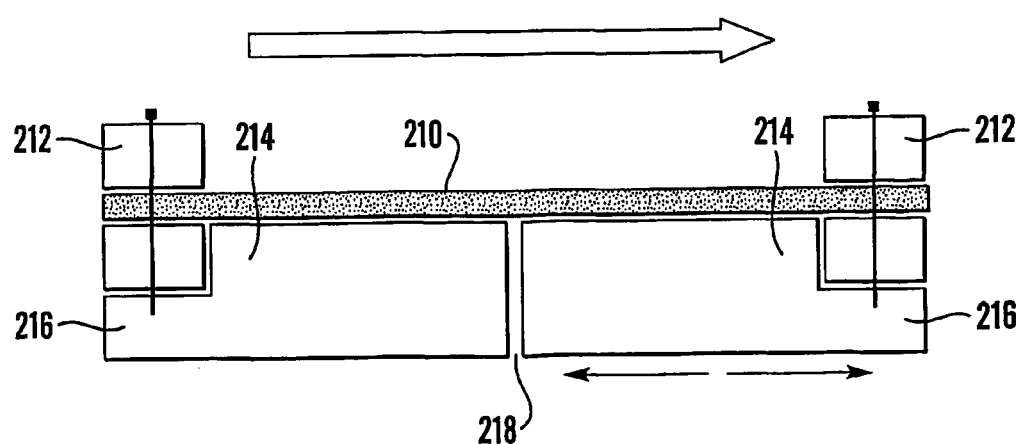
FIG. 2 shows in perspective or sectional elevation or plan sensors in which the test sample acts on polymer composition by way of diffusion.

Referring to FIG. 2(a), a simple contacting head for lengthwise flow of fluid [horizontally or perpendicular to the plane of the paper] comprises a sheet of QTC material 210 supported between metal clamp bars 212 which also are electrodes providing for external electrical connection. The head is installed in a fluid flow channel by fitting over the shoulders 214 of an insulating substrate bar 216 formed on the wall of the channel. Sheet 210 may be pre-stressed to an appropriate level of conductance; alternatively or additionally substrate bar 216 may be split at 218 and provided with means such as a fine screw to adjust the separation of its two parts. A sensor of similar configuration is shown in FIG. 4(c) below.

Figure 2B:
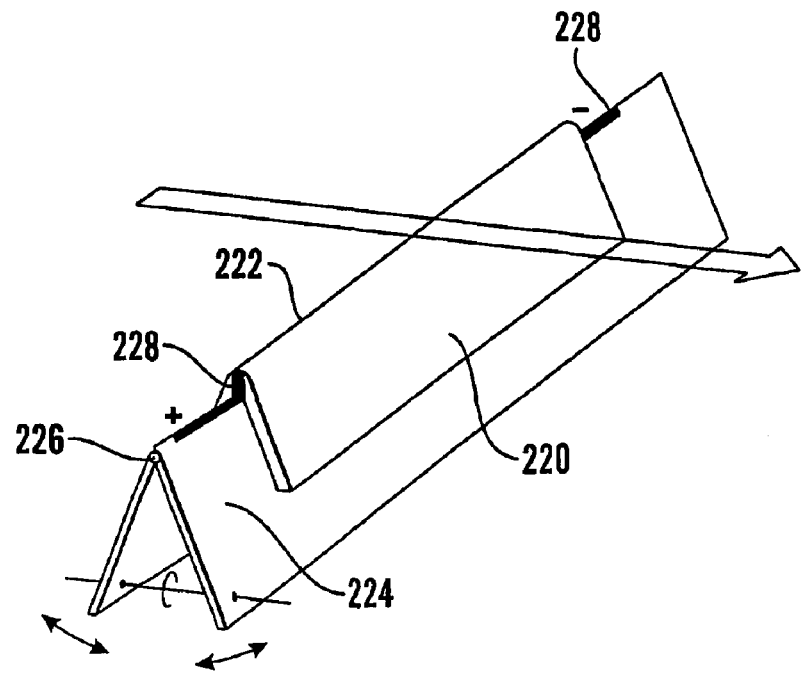

Referring to FIG. 2(b) a fluid flow channel (not shown) carries along at least one wall and transverse to the direction of fluid flow, a series of ridge-shaped members 220 each presenting to the fluid a narrow sensitive region 222 of QTC material in sheet form stretched over non-conductive former 224. Former 224 is hinged at 226 to provide adjustment of the extent of stretch. Each end of narrow region 222 carries an evaporated metal connective member 228, from which an ohmic conductor can be connected to an external electrical circuit. The stretchable polymer composition may be for example nickel in enough silicone rubber to give a self-supporting sheet, or nickel-rich nickel-silicone granules carried by stretchable polymer sheet or foam or textile such as LYCRA™.

Figure 2C:
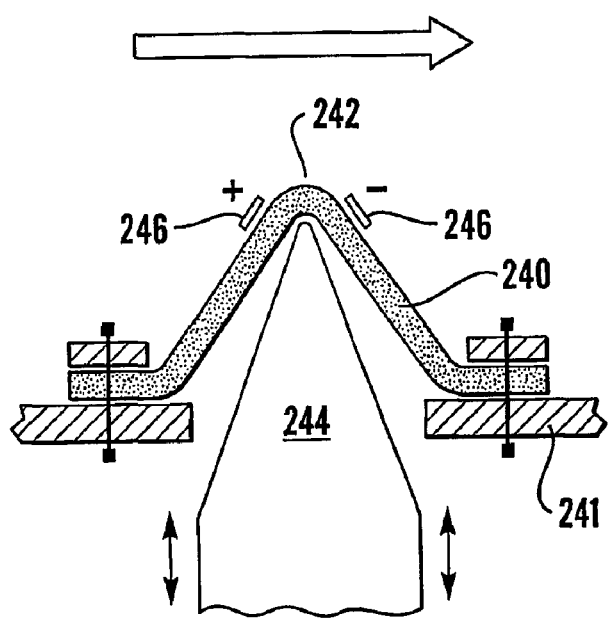

FIG. 2(c) relates to an alternative form of 2(b). Here the ridge-shaped member 240 extends from an aperture in substrate 241, to which it is clamped at its extremities. The sensitive region 242 of member 240 is at the apex of the ridge and the necessary stretch is applied by adjustment of edge former 244. Electrical connection to region 242 is by way of metal electrodes 246 applied by evaporation.

Figure 2D:
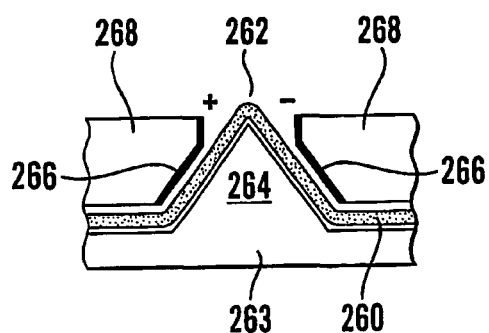
Figure 2F:
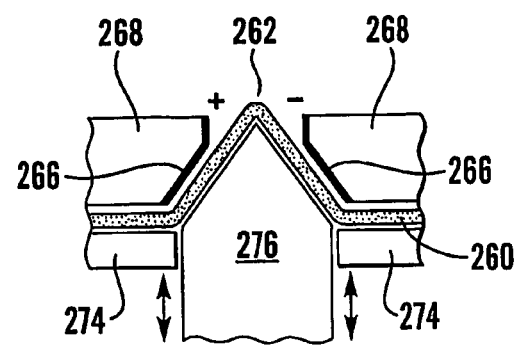

FIG. 2(d) relates to a flow pattern similar to 2(b) and 2(c) but modified to provide the sensitive material in cones instead of ridges. Sheet-form QTC material 260 is shaped and stretched over former 264 projecting through insulating disc 266 to give sensitive region 262 in the path of flowing fluid. The conductance of region 262 is measured between metal electrodes 268 formed on disc 266 by evaporation and bearing on region 262.

Figure 2E:
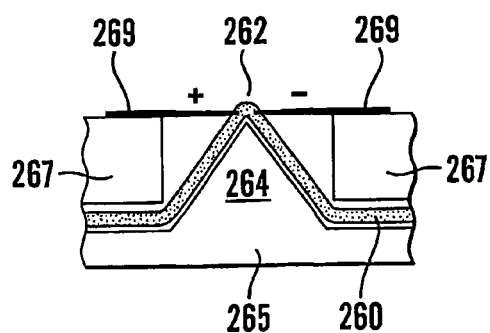
Figure 2G:
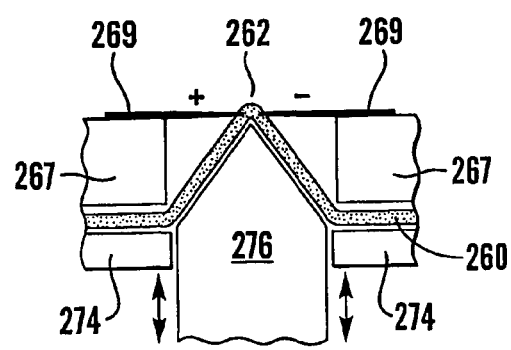

FIG. 2(e) is similar except that the insulating disc, now 267, is formed with a cylindrical aperture, the edges of which support needle electrodes 269 embedded in region 262 of sheet 260.

FIG. 5 below shows how devices according to FIGS. 2(c) to 2(e) can be assembled into a multiple analyser.

FIG. 2(f,g) show modifications in which more scope for stretch adjustment is provided. FIG. 2(f) corresponds to FIG. 2(d) but differs in that substrate 263 carrying conical former 264 is replaced by perforated plate 274 and the function of former 264 is provided by height-adjustable piston 276. FIG. 2(g) differs in the same way from FIG. 2(e). Since piston 276 is structurally separate from plate 274, a sensor using it can with relative ease be modified to fluid through-flow operation, by making it from fluid-permeable material and providing for fluid feed to its lower end.

Figure 2H:
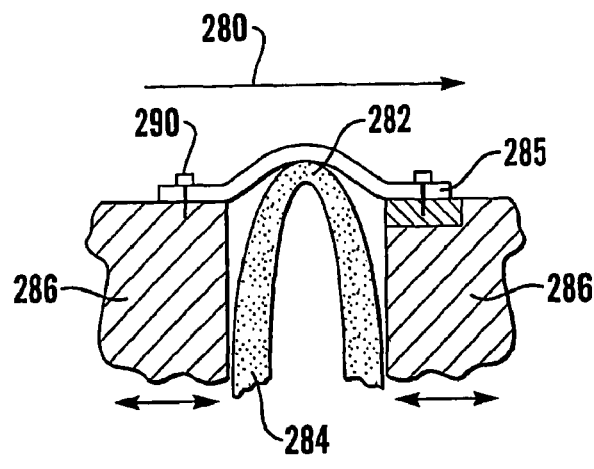
Figure 2I:
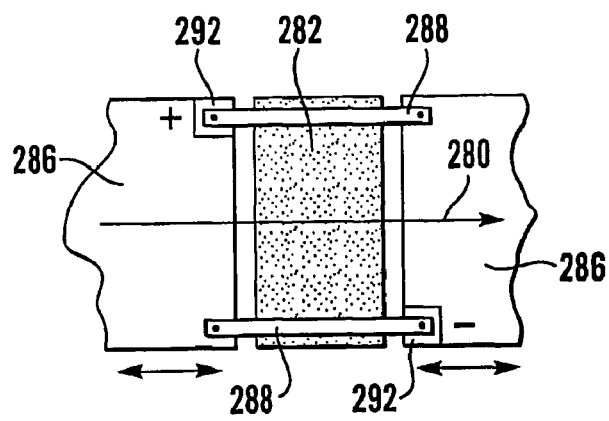

In FIGS. 2(h) (sectional elevation) and 2(i) (plan) the sensor comprises a fluid flow channel 280, a wall of which presents to the fluid one side of a humped area 282, which is the convex end of U-section folded sheet 284 of QTC polymer composition. Sheet 284 projects from a recess bounded by walls 286 and bears against metal electrode bars 288 bridging the recess with sufficient force due to its own elasticity, possibly aided by part-closure of the recess and/or by upward applied force, to make electrical contact. The fold in sheet 284 provides an electrically conductive track between bars 288 by virtue of stretching on its outer side and compression on its inner side. Each bar 288 is electrically connected by bolts 290 to a different side of the recess, with mechanical non-conducting connection to the other side via insulating block 292.

Referring to FIG. 3(a), the sensor comprises a fluid-flow channel 310 indicated generally, carrying at least one head consisting, in order from bottom upwards, of:

rigid substrate 312;

layer 314 of QTC material coated top and bottom with fluid-impermeable metal 316 applied by evaporation as electrodes to be connected to external circuit by wires 318;

thin layer 320 of swellable polymer; and rigid permeable cover 322 made of non-swellable material such as metal or ceramic foam or frit.

Cover 322 is fixed against up-and-down movement between it and rigid substrate 312. In use, fluid diffuses into polymer layer 320 and causes it to swell and compress QTC layer 314, thus increasing its conductance in proportion to the extent of swelling. The specificity of response can be changed by changing polymer layer 320. The sensor can occupy a substantial length of channel 310, or possibly a plurality of heads containing different polymer layers 320 can be disposed along a fluid channel, to provide simultaneous determination of different trace constituents.

FIG. 3(b) shows a sensor on the same principle as 3(a) but with enhanced sensitivity. The area of action of swellable polymer layer is subdivided by struts 313. Between each pair of successive struts 313 is disposed polymer layer 321, overlying block 315 made of conductive material such as metal, tapered downwards to bear on QTC layer 314.

External electrical connections are to each block 315 and via substrate 312 to the evaporatively metal-coated QTC layer 314 as a whole. Since the polymer composition used has zero or low conductance in its plane, layers 321 in this sensor can be of different polymers, for sensitivity to different trace constituents in the fluid.

Referring to FIG. 3(c), the sensor is similar to that of FIG. 1(a), but grid 18 (now numbered 22) is separated from tube 16 and is movable up and down. Grid 22 may comprise electrically conductive material and act as an electrode, but this is not necessary if QTC block 20 carries a conductive coating such as evaporatively applied metal. Above grid 22 is disposed block 24 of permeable swellable polymer as for example random-packed particles, open-cell foam, cloth or honeycomb: such polymer is chosen to be absorptive of, and thus swollen by, a constituent of the fluid to be analysed. Above polymer block 24 is disposed porous ceramic frit 26, distributing the generated stress over block 24. This sensor is used in the same general manner as 1(a). However, particular modes of operation are available:

1. block 24 can remove from the fluid a constituent that is of no interest, thus preventing it from masking other constituents that are to be determined by reference to change of electrical resistance of body 20;
2. block 24 can swell and apply pressure to body 20, thus decreasing its resistance. This enables the sensor to react to a constituent that is inert to the polymer component of body 20, and thus broadens the scope of use of the sensor without changing the polymer component of body 20;
3. if the trace material is present in very low concentration, it may be stored in block 24 over a relatively long time, then expelled by heating (means not shown) over a short time, thus passing a more substantial quantity to body 20 to affect its conductance.

Figure 4A:
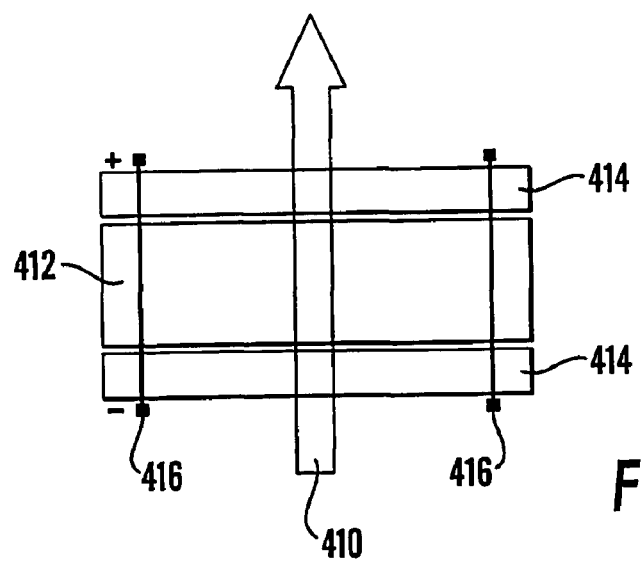
FIG. 4 shows in sectional elevation or perspective sensors based on polymer composition in a specific structural form.

Referring to FIG. 4(a), in a fluid channel indicated generally at 410 is disposed block 412 of fluid-permeable polymer composition consisting of granular QTC nickel/silicone (weight ratio 7:1; volume ratio 0.824:1 of solid nickel within the composition), dispersed in collapsed silicone foam, as described in application PCT/GB/02402). Upstream and downstream of block 412 are placed rigid metal frit electrodes 414, and these are held in contact with block 412 by adjustable bolts 416. Block 412 may be electrically non-conductive or weakly conductive ('start-resistive') as installed, then brought to conductance by compression by tightening bolts 416. Alternatively block 412 may be conductive as installed, for example by more strongly collapsing its foam structure and/or by using initially conductive nickel/silicone of higher nickel content or shrunk during cross-linking: then bolts may be used to increase starting conductance further. Block 412 and electrodes 414 may be supported in an outer sleeve for insertion into flow channel 410, with O-ring seals mating with the wall of the channel.

Figure 4B:
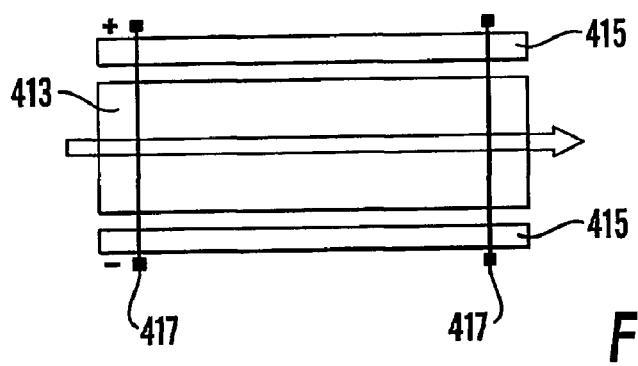
Figure 4C:
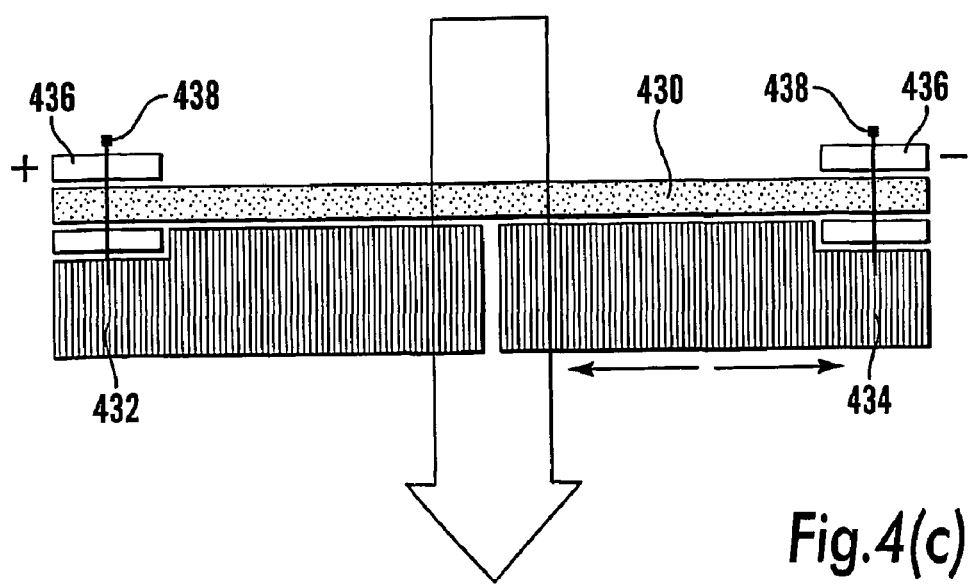

The sensor of FIG. 4(b) is similar to that of FIG. 4(a) but can, owing to longitudinal instead of transverse flow, afford a longer residence time of fluid. The gas flow channel is suitably of rectangular cross-section, at least in the region of the sensor. Block 413 can be of the same composition as in FIG. 4(a) and is disposed between non-permeable metal electrodes 415 with compression adjustable by bolts 417. Alternatively, to fit a cylindrical channel, compression can be adjusted by a worm-driven tubing clip.

A sensor designed to use the principle of FIG. 4(b) is shown in perspective view in FIGS. 4(e) and 4(f) below.

The sensor of FIG. 4(c) affords a relatively short residence time. It is similar to FIG. 2(a) but provides throughflow of fluid. The sensitive element is sheet 430 of foam-supported nickel/silicone QTC granules as in FIG. 4(a), supported by non-conducting fixed substrate 432 and horizontally movable substrate 434, adjustment of which varies stretch and thus conductance of sheet 430. At the extremities of sheet 430 are electrodes 436, clamped into electrical contact with sheet 430 by bolts 438.

Figure 4D:
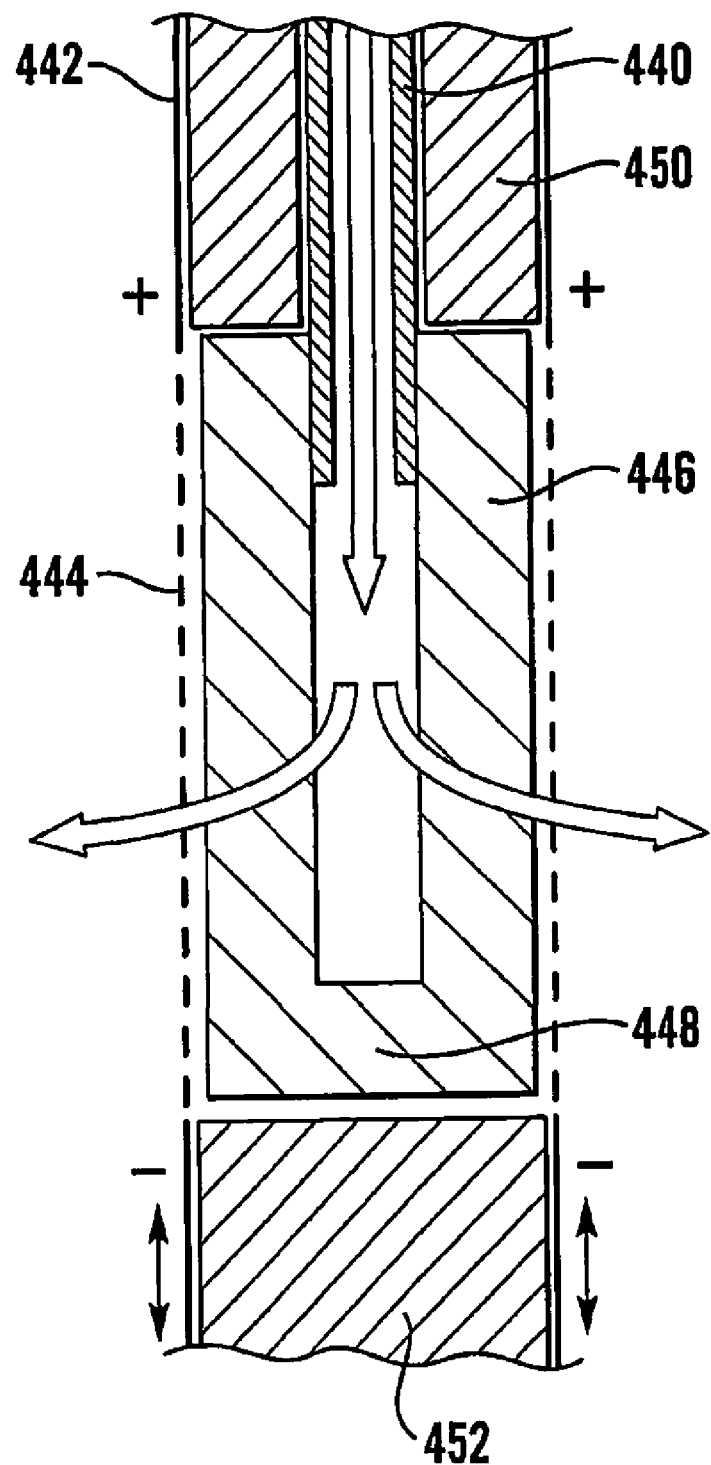
Figure 4E:
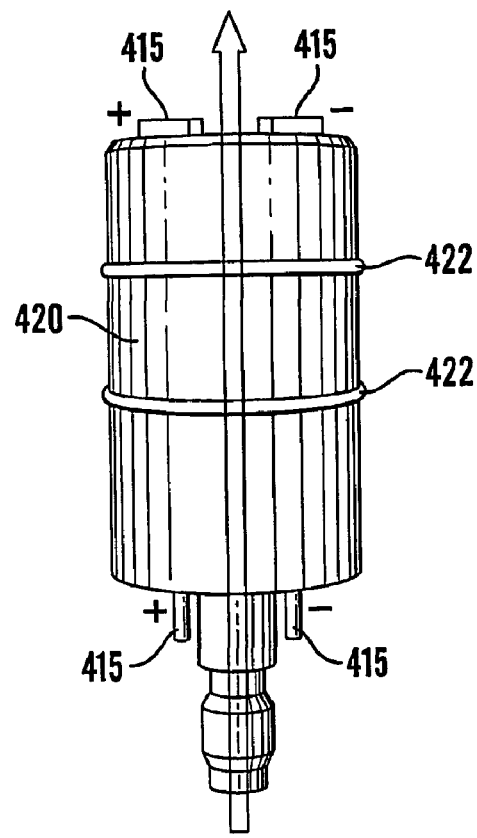
Figure 4F:
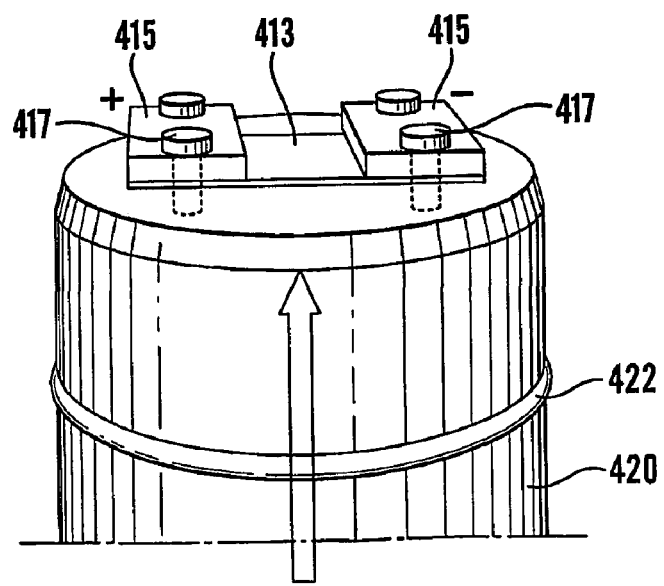

FIG. 4(d) shows a sensor applicable to an outlet pipe 440. It comprises outer framework 442 having fluid-permeable wall region 444, supporting cylindrical block 446 formed internally with axial passage sized to fit snugly over the end of pipe 440 and closed at its downstream end at 448, so that fluid flow is outwardly through region 444. Pipe 440 may be formed with a perforated downward extension controlling the distribution of fluid into block. Block 446 is made of the same foam-supported polymer composition as in FIG. 4(a). Above block 446 and in electrical contact with it is hollow metal cylinder 450 fitting snugly over pipe 440 and fixed in relation to block 446 within framework 442. Below block 446 and in electrical contact with its downstream end 448 is metal cylinder 452, which is movable up and down within framework 442 to adjust the conductance of block 446.

In FIG. 4(e,f) items 413, 415 and 417 correspond to those shown in FIG. 4(b). Electrodes 415 are made of stainless steel and their position in relation to QTC block 413 is adjustable by means of bolts 417. They are removable or replaceable by sliding axially of cylinder 420. The whole unit is assembled in outer cylinder 420, suitably made of 'PERSPEX' acrylic polymer, formed with grooves housing O-rings 422 to form a seal when inserted into a cylindrical fluid flow channel.

Referring to FIG. 5, sketches (a,b) show how devices according to FIGS. 2(c) to 2(e) can be assembled into a multiple analyser. In FIG. 5(a) rigid substrate 263 formed with cones 264 is aligned with QTC sheet 260 and holes 265 of insulating disc 266,267, possibly on a shaft passing through holes 272. The three items are then pressed together.

Figure 5A:
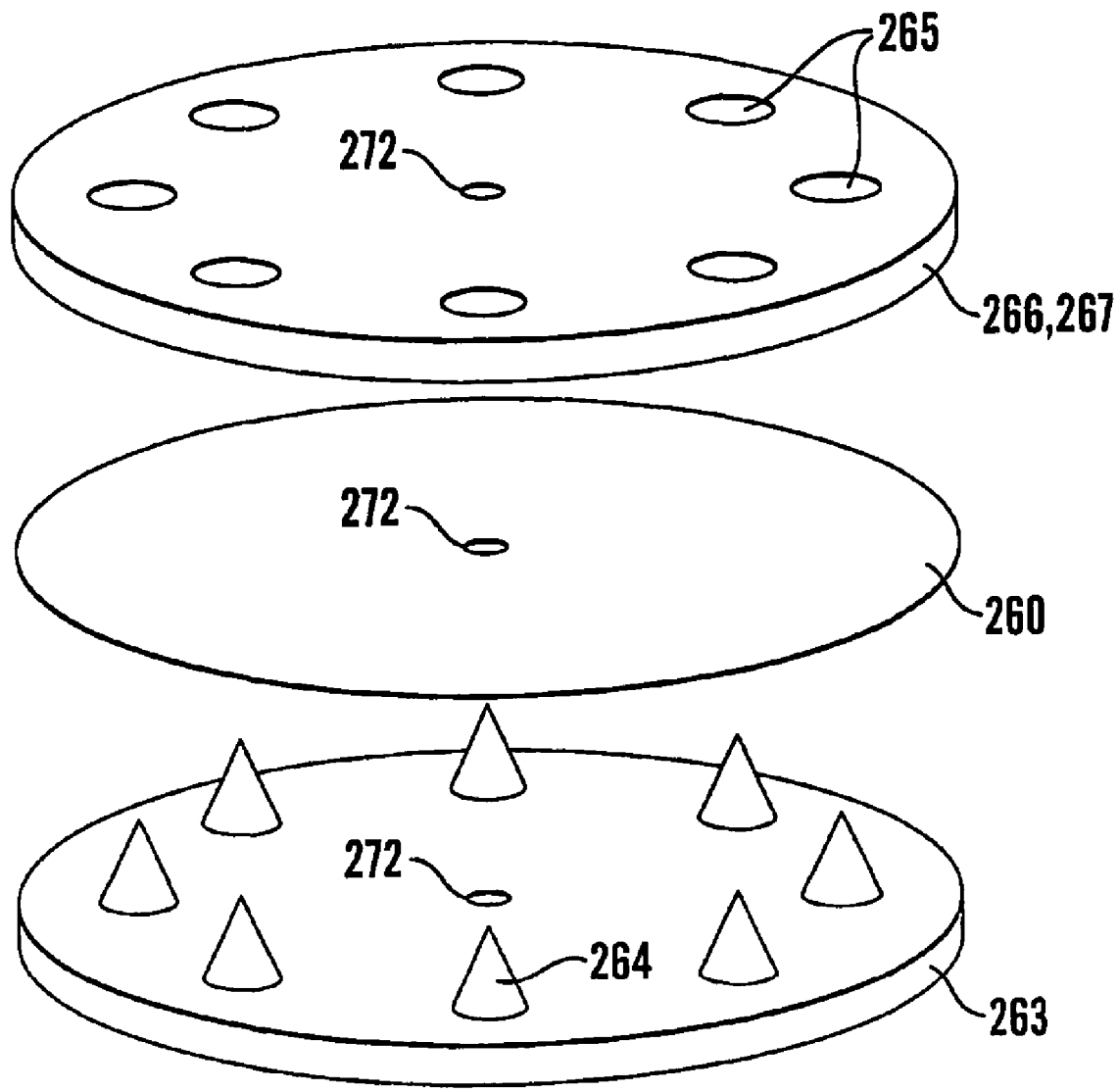
FIG. 5 shows in perspective more complicated laboratory machines based on the sensor.
Figure 5B:
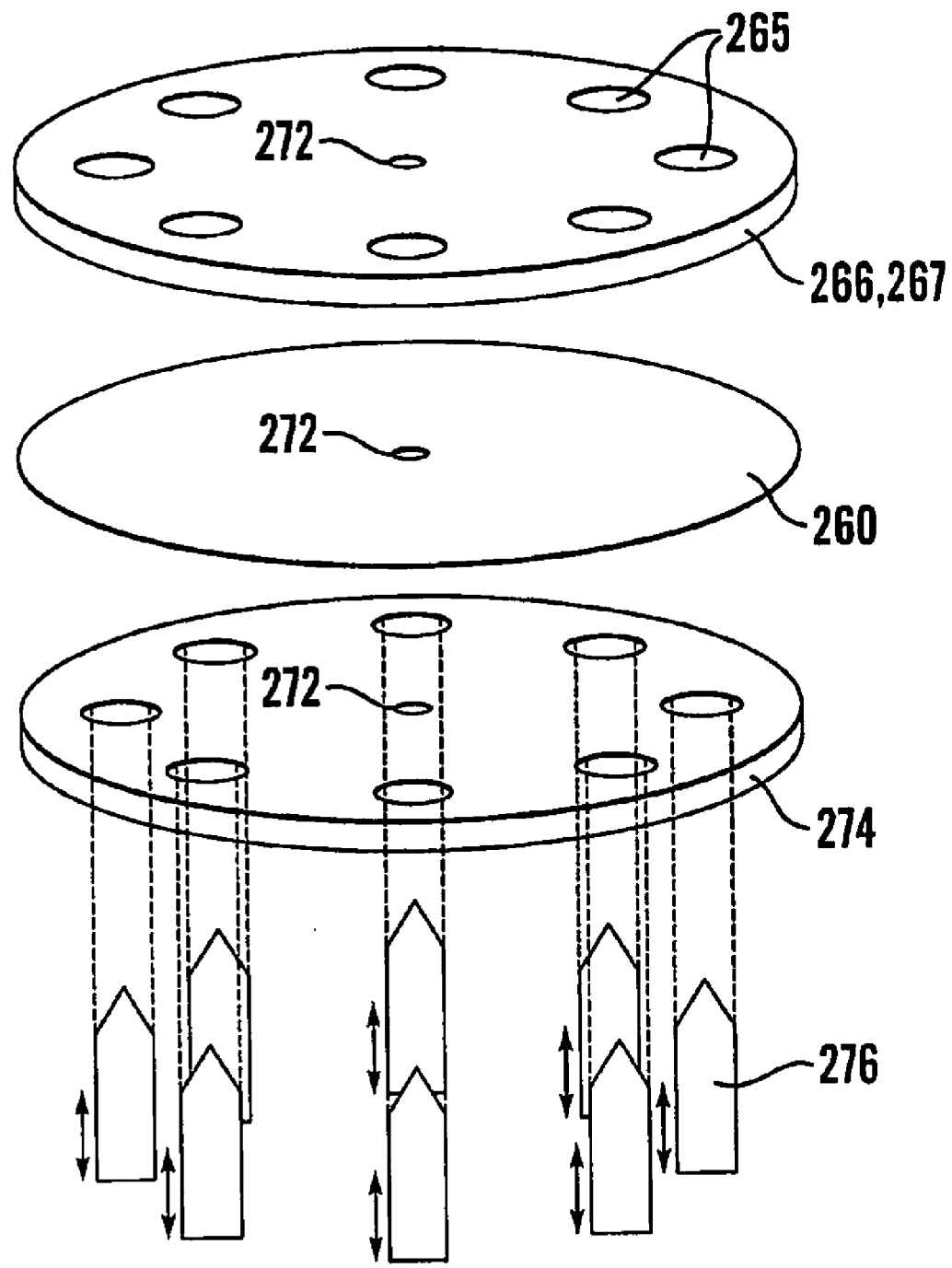

FIG. 5(b) show a modifications of FIG. 5(a) in which more scope for stretch adjustment is provided. Now substrate 263 carrying conical former 264 is replaced by perforated plate 274 and the function of formers 264 is provided by height-adjustable pistons 276. The analyser is assembled in the same way as in FIG. 5(a).

Figure 5C:
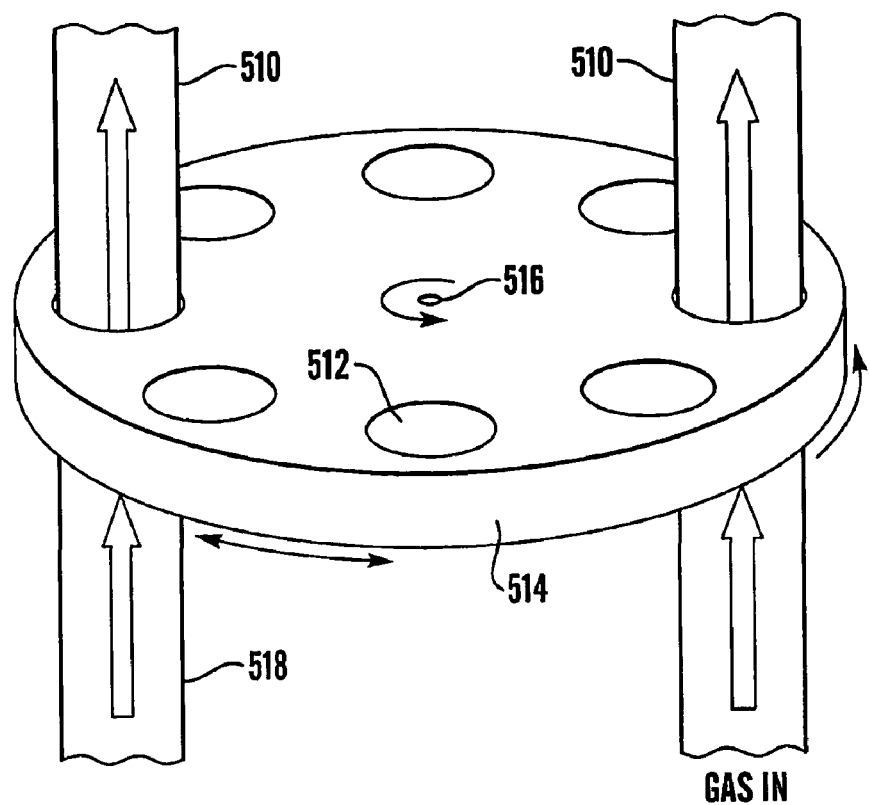

Referring to FIG. 5(c), a miniaturised throughflow sensor 510, such as described with respect to FIG. 1, 3(c) or 4(c), is mounted in each of the holes 512 in disc 514. Disc 514 is rotatable about bearing 516 by powered means (not shown). The fluid inlet 518 of each sensor is fed from a separate source of analyte or from a rotary changeover valve system (not shown). Using such a valve system each sensor can operate in successive phases, for example, sorption, equilibration, desorption/washing.

Figure 5D:
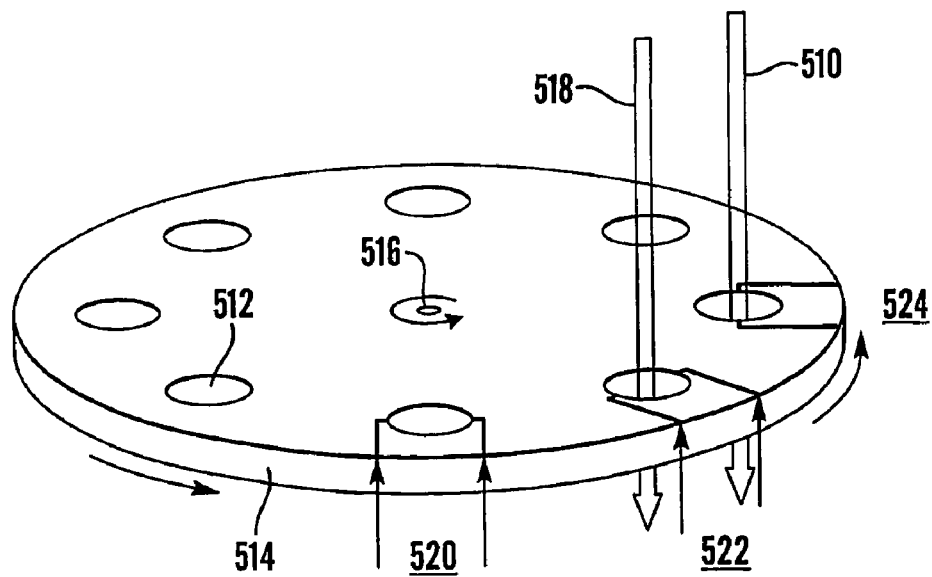

Referring to FIG. 5(d), a system such as that of 5(c) can be operated with electrical instead of or additional to mechanical stress. In position 520 a high voltage pulse applied to the QTC material in sensor 'A' by way of its electrodes induces conductance. Sensor 'A' is then moved to position 522 at which it is connected to a Wheatstone Bridge circuit. Flow of analyte is started and its effect on conductance is measured. At the end of measurement sensor 'A' is moved to position 524 for subsequent phases such as mentioned above, or possibly for electrical reactivation. When sensor 'A' reaches position 522, a further sensor 'B' arrives at position 520 and is activated by high voltage pulse and so on.

FIG. 6 reports the effect of various vapours on conductance. For this operation a contacting unit as described with respect FIG. 1 was used, in which block 20 consisted of QTC polymer composition as follows:

| | |
|---|---|
| conductive filler: | nickel 287 (INCO Corp) |
| polymer | 'SILCOSET 153' (Amber Chemicals: acetoxy-cure silicone rubber with fumed silica reinforcer) |
| nickel:polymer ratio | 8:1 w/w |
| granule size | through 18 mesh, on 50 mesh. |

The contacting unit is connected to a source of dry nitrogen at 1 atm pressure alternatively direct or by way of a bubbler containing the analyte in liquid form. From the upper and lower electrodes 18,14 leads run to a circuit comprising:
  WEIR 4000 voltage source;
  KEITHLEY 2000 multimeter (FET conductance bridge); and
  LabVIEW software in PC.

The test was started up by feeding nitrogen, setting the input electricity supply at 10 volts, 1 mA and adjusting tube 16 until the conductance agreed with the intended input steadily over 15 min. Then the gas feed was switched to pass through a bubbler containing n-hexane. As shown in FIG. 6($a,b$) the resistance increased over 10 min to $10^4$ times its starting value, much of the increase occurring in the first 8 min, corresponding to sorption on the silicone At 40 min the gas feed was switched back to pure nitrogen. The resistance now decreased by a factor of about 100 over 5 min and to its starting value in about 16 min.

The other graphs of FIG. 6 show a similar range of variation of resistance, but differences in speed of sorption or desorption. In other experiments it was observed that the unit is capable of responding to the presence of water vapour in the nitrogen.

The Table reports results for 3 sensors in which, respectively, the nickel conductive filler was dispersed in silicone, polyurethane and polyvinylalcohol. For each determination the QTC was compressed to approximately 20 ohms. The nitrogen flow rate was 50 ml/min, saturated with vapour at room temperature. In each box the resistance in ohms is given for 30 seconds, 60 seconds and saturation (i e no further increase), the times being counted from the start of the change of resistance. It was also observed that on stopping the supply of analyte but continuing pure nitrogen flow, the resistance decreased immediately towards its stating value. The sensor is therefore very effective for showing failure of supply of a desired constituent of a fluid stream.

Referring to FIG. 7, the sensor comprises outer tube 710 formed with a fluid inlet section 712 and outlet section 714. Section 714 is of smaller diameter than 712 and forms an annular shelf 716 at the junction of the sections. It would be equally possible to use a tube of uniform diameter and provide an annular insert. Shelf 716 carries a support grid 718 of electrically insulating material., which in turn carries cylindrical unit 720 of mutually adhering particles each of which is an aggregate of QTC granules coated with shrunk-on thermoset epoxy resin. Unit 720 carries metal terminals 722 for external electrical connection via grommets not shown. Terminals 722 may be separated axially or diametrally. Thus they may consist of metal grids top and bottom, in which event axial pressure is applied to ensure electrical contact. For diametral separation metal electrodes may be for example:
  in contact with the periphery of the unit; or
  drilled into the unit near the periphery; or
  pressed downward on its upper surface near its periphery; or
  pinching the unit near its periphery.

The invention claimed is:

1. A sensor comprising
  i) a conduit for through-flow of a test fluid;
  ii) a porous body of granules of a polymer composition having particles of conductive filler metal, alloy or reduced metal oxide dispersed therein, said body having a first level of electrical conductance when quiescent and being convertible to a second level of conductance by change of stress applied to the body by stretching or compression or electric field, said body being permeable to the test-fluid and disposed across the conduit whereby, in use, said test fluid flows through said body; and
  iii) electrodes connected to said body for connection to an electrical circuit responsive to a change in conductance of said body.

2. A sensor according to claim 1 wherein a bed of granules is supported in the conduit between a pair of perforate grids forming the electrodes.

3. A sensor according to claim 2 wherein at least one of the grids is moveable towards the other whereby the bed can be compressed.

4. A sensor according to claim 3 wherein the porous body is held between clamps forming the electrodes disposed on either side of the conduit.

5. A sensor according to claim 3 wherein the bed of granules comprises a foam or textile having granules of the polymer composition dispersed therein.

6. A sensor according to claim 1 wherein the porous body comprises a sheet and wherein means are provided to stretch the sheet.

7. A sensor according to claim 6 wherein the means to stretch the sheet comprises a hollow member bearing against one surface of the sheet and moveable in a direction perpendicular to the plane of the sheet.

* * * * *